United States Patent [19]

Ehrhardt et al.

[11] Patent Number: 4,889,864
[45] Date of Patent: Dec. 26, 1989

[54] CARBAMOYLIMIDAZOLE DERIVATIVES AND THEIR USE AS FUNGICIDES

[75] Inventors: Heinz Ehrhardt, Rehling; Hilmar Mildenberger, Kelkheim; Thomas Maier, Frankfurt am Main; Rainer Schaller, Gersthofen; Burkhard Sachse, Kelkheim; Peter Braun, Mainz, all of Fed. Rep. of Germany

[73] Assignee: Hoechst Aktiengesellschaft, Frankfurt, Fed. Rep. of Germany

[21] Appl. No.: 127,065

[22] Filed: Dec. 1, 1987

[30] Foreign Application Priority Data

Dec. 3, 1986 [DE] Fed. Rep. of Germany ....... 3641343

[51] Int. Cl.$^4$ .................. C07D 401/06; C07D 403/06; A01N 43/50
[52] U.S. Cl. ..................... 514/326; 514/210; 514/312; 514/314; 514/367; 514/375; 514/397; 540/596; 540/597; 540/603; 540/602; 546/210; 546/157; 546/176; 546/193; 546/194; 548/171; 548/221; 548/229; 548/336
[58] Field of Search ............... 514/210, 312, 314, 326, 514/367, 375, 397; 540/596, 597, 603, 602; 546/210, 187, 176, 193, 194; 548/171, 229, 221, 336

[56] References Cited

U.S. PATENT DOCUMENTS 3,996,366  12/1976  Baker et al. .................. 548/336
4,250,179  2/1981  Birchmore et al. .................. 548/101

Primary Examiner—Robert T. Bond
Attorney, Agent, or Firm—Curtis, Morris & Safford

[57] ABSTRACT

Compounds of the formula (I)

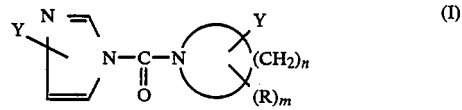

in which
n denotes a number from 2 to 6, m denotes 1 or 2,
R denotes $$-OR^1, -CHO-R^1, -CH-SR^2, -CH_2CHOR^1 \text{ or}$$
$$\phantom{-OR^1, -}\ \ R^2 \phantom{-R^1,}\ \ \ R^2 \phantom{-SR^2, -}\ R^2$$

$$-CH_2CH_2CH_2OR^1,$$

$R^1$ denotes (substituted) alkyl, (substituted) alkenyl, $C_3$-alkynyl, cycloalkyl, cycloalkenyl or an aromatic or heteroaromatic radical, $R^2$ denotes H or alkyl and Y denotes H, alkyl, phenyl or halophenyl, and the metal-salt complexes thereof have advantageous fungicidal actions and are highly suitable for use in plant protection or in the industrial sector.

6 Claims, No Drawings

CARBAMOYLIMIDAZOLE DERIVATIVES AND THEIR USE AS FUNGICIDES

DESCRIPTION

Carbamoylimidazole derivatives, a process for their preparation, and their use as fungicides.

The present invention relates to novel carbamoylimidazole derivatives, a process for their preparation, and their use as plant-treatment agents.

It has already been disclosed that certain carbamoyl derivatives have a fungicidal activity (cf. German Offenlegungsschrift 2,812,662). However, their strength of action, their breadth of action and their tolerability are not completely satisfactory.

It has now been found that novel carbamoyl derivatives do not have these disadvantages.

The invention therefore relates to carbamoylimidazole derivatives of the formula I

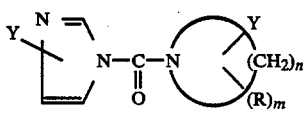

in which
n denotes 2, 3, 4, 5 or 6,
m denotes 1 or 2,
R denotes

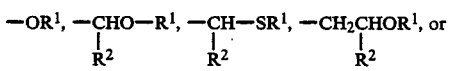

 

$R^1$ denotes ($C_1$–$C_{10}$)-alkyl or ($C_3$–$C_{10}$)-alkenyl, which may in both cases be substituted by 1 to 6 fluorine, chlorine or bromine atoms, hydroxyl, ($C_1$–$C_4$)-alkoxy, phenyl or phenoxy, where the latter two are unsubstituted or substituted by halogen, ($C_1$–$C_4$)alkyl or ($C_1$–$C_4$)alkoxy, or denotes $C_3$-alkynyl, ($C_3$–$C_6$)-cycloalkyl, ($C_5$–$C_6$)-cycloalkenyl, phenyl, benzyl, benzohydryl, trityl, biphenyl, phenoxyphenyl, phenylthiophenyl, naphthyl, 1,2,3,4-tetrahydronaphthyl, indanyl, fluorenyl, pyridyl, benzothiazolyl, benzoxazolyl, quinolinyl, thiochromanyl, benzofuranylmethyl, quinolinylmethyl or phenacyl, where the ring systems mentioned are unsubstituted or substituted by 1-5 substituents from the series comprising halogen, ($C_1$–$C_8$)-alkyl, halo($C_1$–$C_8$)alkyl, ($C_3$–$C_8$)-cycloalkyl, ($C_1$–$C_8$)-alkoxy, halo($C_1$–$C_8$)alkoxy, ($C_3$–$C_8$)-cycloalkyl-($C_1$–$C_4$)alkyl, ($C_1$–$C_8$)alkylthio, halo($C_1$–$C_4$)alkylthio, ($C_1$–$C_8$)alkylsulfinyl, ($C_1$–$C_8$)alkylsulfonyl, $NO_2$, —CN, —CHO or ($C_1$–$C_4$)alkylcarbonyl; or denotes ($C_4$–$C_{10}$)alkadienyl,
$R^2$ denotes H or ($C_1$–$C_4$)alkyl, and
Y, independently of one another, denote H, ($C_1$–$C_4$)alkyl, phenyl or halophenyl,
and the metal-salt complexes thereof.

The halo($C_1$–$C_8$)alkyl or halo($C_1$–$C_8$)alkoxy radicals mentioned contain, in particular, 1 to 9 fluorine or chlorine atoms. Examples which may be mentioned are —$CF_3$, —$C_2F_5$, —$CCl_3$, ω-chlorooctyl, $OCF_3$ and hexafluoropropoxy.

Preferred compounds of the formula I are those in which n denotes 4 or 5 and m denotes 1 or 2, in particular 1. Furthermore, particularly preferred compounds of the formula I are those in which, in addition, R represents $OR^1$, $CH_2OR^1$ or $CH_2CH_2OR^1$ and Y represents H, and $R^1$ denotes phenyl, benzyl, benzohydryl, biphenyl, pyridyl or quinolyl, where the ring systems mentioned are unsubstituted or substituted by 1-3 substituents from the series comprising F, Cl, Br, ($C_1$–$C_3$)-alkyl, halo($C_1$–$C_3$)alkyl, ($C_1$–$C_3$)-alkoxy, halo($C_1$–$C_3$)alkoxy, ($C_1$–$C_3$)-alkylthio, $CF_3S$, $CF_3CH_2S$, $NO_2$, CN, CHO or —$COCH_3$, and the metal-salt complexes thereof.

The present invention relates to the compounds (I) in the form of the free bases or in the form of metal-salt complexes. Complexes which may be mentioned are those with metals of groups Ib, IIb, IVb, VII or VIII of the periodic table, such as copper, zinc, tin or manganese. Such complexes are prepared by generally conventional methods.

The compounds (I) have at least one asymmetrical carbon atom and can therefore be produced as enantiomers and diastereomers. The invention covers both the pure isomers and also mixtures thereof. The mixtures of diastereomers can be resolved into the components by customary methods, for example by selective crystallization from suitable solvents or by chromatography on silica gel or aluminum oxide. Racemates can be resolved into the enantiomers by conventional methods, thus, for example, by salt formation with an optically active acid, separation of the diasteromeric salts and liberation of the pure enantiomers by means of a base.

The invention also relates to a process for the preparation of the compounds of the formula I, wherein
(a) a compound of the formula (II)

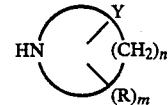

is reacted with a compound of the formula (III)

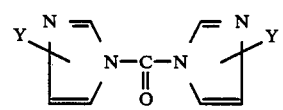

in which Y preferably has the same meaning in both imidazole radicals, if appropriate in the presence of acid accepters and inert solvents, or
(b) a compound of the formula (IV)

is reacted with an imidazole compound of the formula (V)

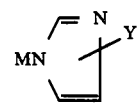

in which M denotes an alkali metal, in particular Na or K, and the compound obtained is converted, if desired, into a metal-salt complex. Some of the compounds of the formula II are known, cf. Bull. Soc. Chim. Fr. (1947) 341, 344; Arch. Pharm. 292 (1959) 165, 167, or can be prepared from the corresponding hydroxyalkylpiperidines by methods which are known to those skilled in the art.

Examples which may be mentioned are:
2-(2-Chlorobenzyloxymethyl)-piperidine, 2-(4-trifluoromethylphenoxymethyl)-piperidine, 2-[2-(4-trifluoromethylphenoxyethyl]-piperidine, 2-[3-(4-trifluoromethylphenoxy)-propyl]piperidine, 4-(4-trifluoromethylphenoxy)-piperidine, 2-[2-chloro-4-trifluoromethylphenoxymethyl]-pyrrolidine, 2-(4-trifluoromethylbenzyloxymethyl)-piperidine and 2-(2,4,6-trichlorophenoxymethyl)-piperidine.

The compounds of the formula IV can be prepared from compounds of the formula I by customary methods. The compounds of the formulae III and V are known from the literature and some are commercially available.

The process for the preparation of the compounds of the general formula (I) in accordance with process variant (a) can expediently be carried out in an inert solvent or diluent. Possible as such are: aliphatic, alicyclic and aromatic hydrocarbons (which may optionally be chlorinated), such as hexane, cyclohexane, petroleum ether, ligroin, benzene, toluene, xylene, methylene chloride, chloroform, carbon tetrachloride, ethylene chloride, trichloroethylene and chlorobenzene; ethers, such as diethyl ether, methyl ethyl ether, di-isopropyl ether, dibutyl ether, propylene oxide, dioxane and tetrahydrofuran; ketones, such as acetone, methyl ethyl ketone, methyl isopropyl ketone and ethyl isobutyl ketone; nitriles, such as acetonitrile, propionitrile and acrylonitrile; alcohols, such as methanol, ethanol, isopropanol, butanol and ethylene glycol; esters, such as ethyl acetate and amyl acetate; acid amides, such as dimethylformamide and dimethylacetamide; sulfones and sulfoxides, such as dimethyl sulfoxide and sulfolane; and bases, such as pyridine.

Reaction variant (a) is carried out, if appropriate, in the presence of an acid acceptor. Examples of such acid acceptors include the hydroxides, carbonates, hydrogen carbonates and alcoholates of alkali metals, in particular of Na and K, or tertiary amines, such as triethylamine, diethylaniline and pyridine.

Reaction variant (a) can be carried out within a broad temperature range. In general, it is carried out at a temperature between about $-20°$ C. and the boiling point of the reaction mixture, preferably between $0°$ C. and about $100°$ C. The reaction is preferably carried out under normal atmospheric pressure; however, it is also possible to work under increased or reduced pressure.

Reaction variant (b) according to the present invention is preferably carried out in the presence of an inert solvent or diluent. The solvents or diluents specified under (a) are used. Reaction variant (b) is preferably carried out in the presence of acid acceptors. Examples of such acid acceptors include the hydroxides, carbonates, hydrogen carbonates and alcoholates of alkali metals, and tertiary amines, such as triethylamine, diethylaniline and pyridine.

Reaction variant (b) can be carried out within a broad temperature range, for example at a temperature between about $-20°$ C. and the boiling point of the reaction mixture, preferably between $0°$ C. and $100°$ C. Reaction variant (b) is carried out at atmospheric pressure, but it is also possible to work under increased or reduced pressure.

The compounds of the formula I according to the invention are distinguished by an excellent fungicidal action. Even fungal pathogens which have already penetrated into the vegetative tissue can be curatively combated successfully. This is particularly important and advantageous in fungal diseases which can no longer be effectively combated after the infection has arisen using the fungicides which are otherwise conventional. The range of action of the compounds claimed covers a large number of various economically important, phytopathogenic fungi, such as, for example, *Piricularia oryzae*, true mildew species, Fusarium species, *Plasmopora viticola*, *Pseudoperonospora cubensis*, various rust fungi and *Pseudocercosporella herpotrichoides*. Benzimidazole- and dicarboximide-sensitive and -resistant *Botrytis cinerea* strains are combated particularly well.

The compounds of the formula I are also suitable for use in industrial areas, for example as wood-protection agents, as preservatives in paints, in cooling lubricants for metalworking or as preservatives in drilling and cutting oils.

The present invention therefore also relates to fungicides which contain a compound of the formula I besides suitable auxiliaries.

The agents can be used in conventional preparations as wettable powders, emulsifiable concentrates, sprayable solutions, dusts, dressings, dispersions, granules or microgranules.

Wettable powders are preparations which are uniformly dispersable in water and which contain, besides the active compound and in addition to, if appropriate, a diluent or insert substance, also wetting agents, for example polyoxyethylated alkylphenols, polyoxyethylated fatty alcohols, alkylsulfonates or alkylphenylsulfonates and dispersants, for example sodium ligninsulfonate, sodium 2,2'-dinaphthylmethane-6,6'-disulfonate, sodium 2,2'-dibutylnaphthalenesulfonate or sodium oleoylmethyltaurinate. They are prepared in a conventional fashion, for example by grinding and mixing the components.

Emulsifiable concentrates can be produced, for example, by dissolving the active compound in an inert organic solvent, for example, butanol, cyclohexanone, dimethylformamide, xylene or higher-boiling aromatics or hydrocarbons, with addition of one or more emulsifiers. In the case of liquid active compounds, all or part of the solvent can be omitted. Emulsifiers which can be used are, for example: calcium salts of alkylarylsulfonic acid, such as Ca-dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, alkyl polyglycol ethers, sorbitan fatty acid esters, polyoxyethylene sorbitan fatty acid esters or polyoxyethylene sorbitol esters.

Dusts are obtained by grinding the active compound with finely divided solid substances, for example talc or natural clays, such as kaolin, bentonite, poryphillite or diatomaceous earth.

Granules can be produced either by spraying the active compound onto to adsorptive, granulated inert material, or by applying active compound concentrates onto the surface of excipients such as sand, kaolinite or granulated inert material by means of binders, for example polyvinyl alcohol, sodium polyacrylate or alternatively mineral oils. Suitable active compounds can also be granulated in the fashion which is conventional for the preparation of fertilizer granules—if desired as a mixture with fertilizers.

The active compound concentration in wettable powders is, for example, about 10 to 90% by weight; the remainder to 100% by weight comprises conventional formulation components. In the case of emulsifiable concentrates, the active compound concentration can be about 10 to 80% by weight.

Dust-form formulations usually contain 5 to 20% by weight of active compound, sprayable solutions about 2 to 20% by weight. In the case of granules, the active compound content depends partly on whether the active compound is liquid or solid and on which granulation auxiliaries, fillers etc. are used.

In addition, the active compound formulations mentioned contain, if appropriate, the adhesives, wetting agents, dispersants, emulsifiers, penetrants, solvents, fillers or excipients which are conventional in each case.

The application rates of the compounds according to the invention generally vary between 0.01 and 2.0 kg/ha, in particular between 0.05 and 1.5 kg/ha.

For use, the concentrates, present in commercially available form, are diluted, if appropriate, in a conventional fashion, for example using water in the case of wettable powders, emulsifiable concentrates, dispersions and, in some cases, also in the case of microgranules. Dust-form and granulated preparations and also sprayable solutions are usually not further diluted with inert substances before use.

Mixtures or mixed formulations of the compounds of the formula I, in particular those of the following examples, can be used with other active compounds, such as, for example, insecticides, acaricides, herbicides, fertilizers, growth regulators or fungicides, it being possible to achieve synergistic increases in action in some cases.

Suitable fungicidal combination partners are, for example, the active compounds imazalil, prochloraz, fenapanil, SSF105, triflumizole, PP969, flutriafol, BAY-MEB 6401, propiconazole, etaconazole, diclobutrazole, bitertanol, triadimefon, triadimenol, fluotrimazole, tridermorph, dodemorph, fenpropimorph, falimorph, S-32165, clobenzthiazone, parinol, buthiobate, fenpropidine, triforine, fenarimol, nuarimol, triarimol, ethirimol, dimethirimol, bupirimate, rabenzazole, tricyclazole, ofurace, furalaxyl, benalaxyl, metalaxyl, pencyuron, oxadixyl, cyprofuram, dichlomezin, probenazole, fluobenzimine, pyroxyfur, NK-483, PP-389, pyroquilon, hymexazole, fenitropan, UHF-8227, tolclofos-methyl, ditalimfos, edifenphos, pyrazophos, isoprothiolane, cymoxanil, dichloruanid, captafol, captan, folpet, tolylfluanid, chlorothalonil, etridiazole, iprodione, procymidone, vinclozolin, metomeclan, myclozolin, dichlozolinate, fluorimide, drazoxolon, chinomethionat, nitrothal-isopropyl, dithianon, dinocap, binapacryl, fentin acetate, fentin hydroxide, carboxin, oxycarboxin, pyracarbolid, methfuroxam, fenfuram, furmecyclox, benodanil, mebenil, mepronil, flutolanil, fuberidazole, thiabendazole, carbendazim, benomyl, thiofanate, thiofanate-methyl, CGD-94240F, IKF-1216, mancozeb, maneb, zineb, nabam, thiram, probineb, prothiocarb, propamocarb, dodine, guazatine, dichloran, quintozene, chloroneb, tecnazene, biphenyl, anilazine, 2-phenylphenol, copper compounds, such as Cuoxychloride, Cu oxine and Cu oxide, sulfur and fosetyl-aluminum, sodium dodecylbenzenesulfonate, sodium dodecylsulfate, sodium C13/C15-alcohol ether sulfonate, sodium cetostearylphosphate ester, sodium dioctyl sulfosuccinate, sodium isopropylnaphthalenesulfonate, sodium methylenebisnaphthalenesulfonate, cetyltrimethylammonium chloride, salts of long-chain primary, secondary or tertiary amines, alkylpropyleneamines, laurylpyridinium bromide, ethoxylated quaternary fatty amines, alkyldimethylbenzylammonium chloride and 1-hydroxyethyl-2-alkylimidazoline.

The combination partners mentioned are all known compounds, the majority of which are described in C. R. Worthing and S. B. Walker, The Pesticide Manual, 7th edition (1983), British Crop Protection Council. Compounds for which numerical codes are given have the following structures:

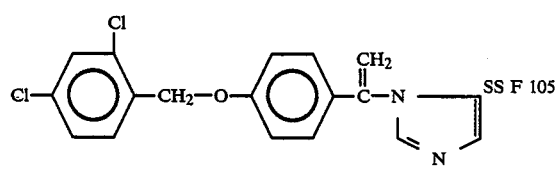

SS F 105

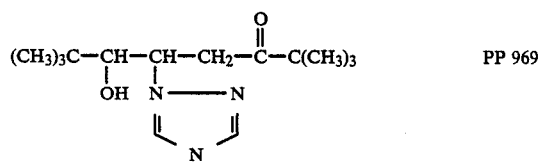

PP 969

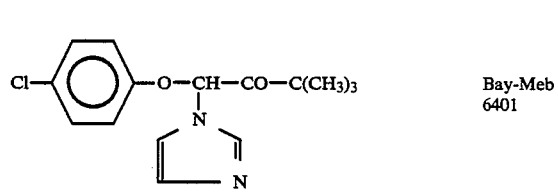

Bay-Meb 6401

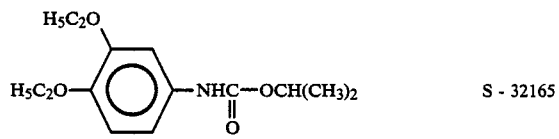

S - 32165

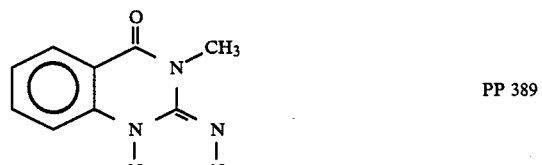

PP 389

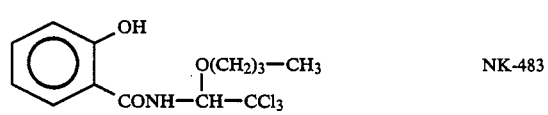

NK-483

The invention is described by the following examples:

A. FORMULATION EXAMPLES

Example 1

A dust was obtained by mixing
10 parts by weight of active compound and
90 parts by weight of talc
as inert material and comminuting the mixture in a hammer mill.

Example 2

A wettable powder which was easily dispersable in water is obtained by mixing
- 25 parts by weight of active compound,
- 64 parts by weight of kaolin-containing quartz as inert material,
- 10 parts by weight of potassium ligninsulfonate and
- 1 part by weight of sodium oleoylmethyltaurinate as wetting and dispersing agent, and grinding the mixture in a pin disk mill.

Example 3

A dispersion concentrate which is easily dispersable in water was obtained by mixing
- 20 parts by weight of active compound with
- 6 parts by weight of alkylphenol polyglycol ether (®Triton X 207)
- 3 parts by weight of isotridecanol polyglycol ether (8 EO) and
- 71 parts by weight of paraffinic mineral oil (boiling range, for example, about 255° to above 377° C.), and grinding the mixture in a ball mill to a fineness of below 5 microns.

Example 4

An emulsifiable concentrate is obtained from
- 15 parts by weight of active compound,
- 75 parts by weight of cyclohexanone as solvent and
- 10 parts by weight of oxyethylated nonylphenol (10 EO) as emulsifier.

B. CHEMICAL EXAMPLES

Example 1

2-(2-Chlorobenzyloxymethyl)-1-(1-imidazolylcarbamoyl)piperidine 5.50 g (0.034 mol) of Carbonyldiimidazole were added to 8.00 g. (0.033 mol) of 2-(2-chlorobenzyloxymethyl)-piperidine, dissolved in 50 ml of toluene, and the mixture was warmed at 50° C. for 4 hours. After cooling, the mixture was washed with $2 \times 30$ ml of water, the solvent was removed by distillation in vacuo. 9.20 g (84%) of the title compound were obtained as slightly yellowish crystals of melting point 91°-2° C.

The compounds of the formula I from the following table can be prepared in an analogous fashion, Y in each case being hydrogen.

| Example No. | n | $(R)_m$ | m.p. (°C.) |
|---|---|---|---|
| 2 | 5 | $2\text{-}CH_2OCH_2CH=CH\text{-}C_6H_5$ | oil |
| 3 | 5 | $2\text{-}CH_2OCH_2\text{-}C(CH_3)=CHCH_2CH_2CH=C(CH_3)_2$ | oil |
| 4 | 5 | $2\text{-}CH_2OCH_2C=CH_2$ | |
| 5 | 5 | $2\text{-}CH_2O\text{-}cyclo\text{-}C_6H_{11}$ | |
| 6 | 5 | $3\text{-}CH_2O\text{-}C_6H_4\text{-}4\text{-}CF_3$ | |
| 7 | 5 | $3\text{-}O\text{-}C_6H_4\text{-}4\text{-}CF_3$ | oil |
| 8 | 5 | $3\text{-}O\text{-}C_6H_3\text{-}2\text{-}Cl, 4\text{-}CF_3$ | |
| 9 | 5 | $4\text{-}O\text{-}C_6H_4\text{-}4\text{-}CF_3$ | 103-4 |
| 10 | 5 | $3\text{-}CH_2O\text{-}C_6H_4\text{-}4\text{-}CF_3$ | oil |
| 11 | 5 | $3\text{-}CH_2O\text{-}CH_2C_6H_2\text{-}2,4,6\text{-}Cl_3$ | oil |
| 12 | 5 | $3\text{-}CH_2O\text{-}C_6H_4\text{-}2\text{-}Cl,4\text{-}CF_3$ | oil |
| 13 | 5 | $3\text{-}OC_6H_4\text{-}3\text{-}CF_3$ | |
| 14 | 5 | $3\text{-}OC_6H_2\text{-}2,4,6\text{-}Cl_3$ | |
| 15 | 5 | $3\text{-}OC_6H_3\text{-}2\text{-}Cl,4\text{-}CF_3$ | |
| 16 | 5 | $3\text{-}OCH_2\text{-}C_6H_2\text{-}2,4,6\text{-}Cl_3$ | oil |
| 17 | 5 | $2\text{-}CH_2OC_6H_4\text{-}4\text{-}CF_3$ | oil |
| 18 | 5 | $2\text{-}CH_2OC_6H_3\text{-}2\text{-}Cl,4\text{-}CF_3$ | oil |
| 19 | 5 | $2\text{-}CH_2OC_6H_2\text{-}2,6\text{-}Cl_2\text{-}4\text{-}CF_3$ | oil |
| 20 | 5 | $2\text{-}CH_2OC_6H_2\text{-}2,4,6\text{-}Cl_3$ | |
| 21 | 5 | $2\text{-}CH_2OC_6H_3\text{-}2,4\text{-}Cl_2$ | |
| 22 | 5 | $2\text{-}CH_2OC_6H_4\text{-}4\text{-}Cl$ | |
| 23 | 5 | $2\text{-}CH_2OC_6H_4\text{-}4\text{-}F$ | |
| 24 | 5 | $2\text{-}CH_2OC_6H_3\text{-}2,4\text{-}F_2$ | |
| 25 | 5 | $2\text{-}CH_2SC_6H_4\text{-}4\text{-}Cl$ | oil |
| 26 | 5 | $2\text{-}CH_2O\text{-}C_6H_4\text{-}2\text{-}CF_3$ | oil |
| 27 | 5 | $2\text{-}CH_2O\text{-}C_6H_3\text{-}3\text{-}Cl,4\text{-}CF_3$ | oil |
| 28 | 5 | $2\text{-}CH_2OCH_2C_6H_2\text{-}2,4,6\text{-}Cl_3$ | oil |
| 29 | 5 | $2\text{-}CH_2OCH(C_6H_5)_2$ | oil |
| 30 | 5 | $2\text{-}CH_2CH_2O\text{-}C_6H_4\text{-}4\text{-}CF_3$ | oil |
| 31 | 5 | $2\text{-}CH_2CH_2O\text{-}C_6H_4\text{-}2\text{-}CF_3$ | oil |
| 32 | 5 | $2\text{-}CH_2CH_2O\text{-}C_6H_3\text{-}3\text{-}Cl,4\text{-}CF_3$ | oil |
| 33 | 5 | $2\text{-}CH_2OC_6H_3\text{-}2\text{-}CN,3\text{-}F$ | oil |
| 34 | 5 | $2\text{-}CH_2OCH_2C_6H_4\text{-}4Cl$ | oil |
| 35 | 5 | $2\text{-}CH_2OCH_2C_6H_4\text{-}4\text{-}CF_3$ | oil |
| 36 | 5 | $2\text{-}CH_2OCH[C_6H_4\text{-}4F][C_6H_3\text{-}2,4\text{-}Cl_2]$ | oil |
| 37 | 5 | $2\text{-}CH(CH_3)\text{-}OC_6H_4\text{-}4\text{-}CF_3$ | oil |
| 38 | 5 | $2\text{-}CH_2CH(CH_3)\text{-}O\text{-}C_6H_4\text{-}4\text{-}CF_3$ | oil |
| 39 | 4 | $2\text{-}CH_2O\text{-}C_6H_3\text{-}2,6\text{-}Cl_2$ | oil |
| 40 | 4 | $2\text{-}CH_2OCH_2\text{-}C_6H_2\text{-}2,4,6\text{-}Cl_3$ | oil |
| 41 | 4 | $2\text{-}CH_2O\text{-}C_6H_3\text{-}2,6\text{-}Cl_2,4\text{-}CF_3$ | oil |
| 42 | 4 | $2\text{-}CH_2O\text{-}C_6H_4\text{-}4\text{-}CF_3$ | oil |
| 43 | 4 | $2\text{-}CH_2O\text{-}C_6H_4\text{-}2\text{-}CF_3$ | |
| 44 | 4 | $2\text{-}CH_2O\text{-}C_6H_4\text{-}2\text{-}Cl,4\text{-}CF_3$ | oil |
| 45 | 5 | $2,3\text{-}bis\text{-}(CH_2O\text{-}C_6H_4\text{-}4CF_3)$ | |
| 46 | 5 | $2,6\text{-}bis\text{-}(CH_2O\text{-}C_6H_4\text{-}4\text{-}CF_3)$ | |
| 47 | 5 | $2\text{-}CH_2O\text{-}(2\text{-}pyridyl\text{-}5\text{-}CF_3)$ | oil |
| 48 | 5 | $2\text{-}CH_2O\text{-}(2\text{-}pyridyl\text{-}3\text{-}Cl,5\text{-}CF_3)$ | oil |
| 49 | 5 | $2\text{-}CH_2O\text{-}(2\text{-}pyridyl\text{-}3\text{-}CF_3,5\text{-}Cl)$ | |
| 50 | 5 | $2\text{-}CH_2O\text{-}(2\text{-}pyridyl)$ | 83-5 |

-continued

| Example No. | n | (R)$_m$ | m.p. (°C.) |
|---|---|---|---|
| 51 | 5 | 2-CH$_2$O—(2-pyridyl-5-Br) | 97–101 |
| 52 | 5 | 2-CH$_2$O—(2-pyridyl-6-Cl) | 67–75 |
| 53 | 5 | 2-CH$_2$CH$_2$O—(2-pyridyl) | oil |
| 54 | 5 | 2-CH$_2$CH$_2$O—(2-pyridyl-5-Br) | oil |
| 55 | 5 | 2-CH$_2$CH$_2$O—(2-pyridyl-5-Cl) | 70–4 |
| 56 | 5 | 2-CH$_2$CH$_2$O—(2-pyridyl-5,6-(CH$_3$)$_2$) | 64–6 |
| 57 | 5 | 2-CH$_2$CH$_2$O—(2-pyridyl-6-Cl) | oil |
| 58 | 5 | 4-O—(2-pyridyl-6-Cl) | 149–52 |
| 59 | 5 | 4-O—(2-pyridyl) | 80–2 |
| 60 | 6 | 2-CH$_2$O—C$_6$H$_4$—4-CF$_3$ | |
| 61 | 5 | 2-CH$_2$O—(6-Cl—benzoxazol-2-yl) | |
| 62 | 5 | 2-CH$_2$O—(6-Cl—benzthiazol-2-yl) | |
| 63 | 5 | 2-CH$_2$O-(quinolinyl) | |
| 64 | 5 | 2-CH$_2$O-(3-Cl-benzofuran-2-yl) | |
| 65 | 3 | 2-CH$_2$OC$_6$H$_4$—4-CF$_3$ | |
| 66 | 6 | 2-CH$_2$OC$_6$H$_4$—4-CF$_3$ | |
| 67 | 5 | 2-CH$_2$OCH$_2$—C$_6$H$_3$—2-F,4-Cl | oil |
| 68 | 5 | 2-CH$_2$OCH$_2$—OC$_6$H$_4$—2-Cl | oil |
| 69 | 5 | 2-CH$_2$OCH$_2$—C$_6$H$_4$—4-F | oil |
| 70 | 5 | 2-CH$_2$CH(CH$_3$)O—C$_6$H$_3$—3-Cl,4-CF$_3$ | oil |
| 71 | 5 | 3-OC$_6$H$_3$—3-Cl,4-CF$_3$ | oil |
| 72 | 5 | 2-CH$_2$OCH$_2$—C$_6$H$_3$—3,4-Cl$_2$ | 82–4 |
| 73 | 5 | 2-CH$_2$OCH$_2$—C$_6$H$_3$—2,4-Cl$_2$ | 110–2 |
| 74 | 4 | 2-CH$_2$O—C$_6$H$_3$—2-F,4-CF$_3$ | oil |
| 75 | 5 | 2-CH$_2$O—C$_6$H$_3$—2-F,4-CF$_3$ | oil |
| 76 | 5 | 2-CH$_2$OCH$_2$-(3-Cl-benzofuran-2-yl) | oil |
| 77 | 5 | 2-CH$_2$OCH$_2$CH=CHCH$_3$ | oil |
| 78 | 5 | 2-CH$_2$OCH$_2$CH=CCl—C$_6$H$_3$—2,4-Cl$_2$ | oil |
| 79 | 5 | 2-CH$_2$OCH$_2$CH=CCl—C$_6$H$_4$—4-Cl | oil |
| 80 | 5 | 2-CH$_2$OCH$_2$CH=CCl—C$_6$H$_5$ | oil |
| 81 | 5 | 2-CH$_2$OCH(CH$_3$)—C$_6$H$_5$ | oil |
| 82 | 5 | 2-CH$_2$OCH$_2$O=CCl—C$_6$H$_4$—4-CH$_3$ (dioxolane) | oil |
| 83 | 5 | 2-CH$_2$—OCH$_2$C$_6$H$_3$—3,5-Cl$_2$ | oil |
| 84 | 5 | 2-CH$_2$OCH$_2$—1-naphthyl | oil |
| 85 | 5 | 2-CH$_2$OCH$_2$C(CH$_3$)=CH$_2$ | oil |
| 86 | 5 | 2-CH$_2$OC$_4$H$_9$(n) | oil |
| 87 | 5 | 2-CH$_2$OCOCH=CH—C$_6$H$_5$ | oil |
| 88 | 5 | 2-CH$_2$CH$_2$OC$_6$H$_3$—2Cl—4-CF$_3$ | oil |
| 89 | 5 | 2-CH$_2$CH$_2$OC$_6$H$_3$—2F—4-CF$_3$ | oil |
| 90 | 5 | 2-CH$_2$CH$_2$OCH$_2$CH=CH—C$_6$H$_5$ | oil |
| 91 | 5 | 2-CH$_2$CH$_2$O(-2-pyridyl-3-Cl—5-CF$_3$) | oil |
| 92 | 5 | 2-CH$_2$CH(CH$_3$)OCH$_2$—C$_6$H$_4$—4-F | oil |
| 93 | 5 | 2-CH$_2$CH(CH$_3$)OCH$_2$C$_6$H$_2$—2,4,6-Cl$_3$ | oil |
| 94 | 5 | 2-CH$_2$CH$_2$OCH$_2$C$_6$H$_4$—4-Cl | oil |
| 95 | 5 | 2-CH$_2$CH$_2$OCH$_2$C$_6$H$_3$—2-F,4-Cl | oil |
| 96 | 5 | 2-CH$_2$CH$_2$OCOC$_6$H$_5$ | oil |
| 97 | 5 | 2-CH$_2$OC$_6$H$_3$—2-CF$_3$,4-Cl | oil |
| 98 | 5 | 2-CH$_2$CH$_2$OC$_6$H$_3$—2-CF$_3$,4-Cl | oil |
| 99 | 5 | 2-CH$_2$CH$_2$OC$_6$H$_2$,2-Cl,4-CF$_3$,6-F | oil |
| 100 | 5 | 2-CH$_2$CH$_2$OC$_6$H$_2$—2,6-Cl$_2$,4-CF$_3$ | oil |
| 101 | 5 | 2-CH$_2$CH$_2$OCH$_2$OC$_6$H$_3$—2,4-Cl$_2$ | oil |
| 102 | 5 | 2-CH$_2$CH$_2$OCH$_3$—1-naphthyl | oil |
| 103 | 5 | 2-CH$_2$CH(CH$_3$)O—C$_6$H$_4$—2-Cl,4-CF$_3$ | |
| 104 | 5 | 2-CH$_2$CH$_2$OCOCH=CH—C$_6$H$_5$ | |
| 105 | 5 | 2-CH$_2$CH$_2$O—(2-quinolyl) | |

-continued

| Example No. | n | (R)$_m$ | m.p. (°C.) |
|---|---|---|---|
| 106 | 5 | 2-CH$_2$CH$_2$O—(2-quinoxalinyl-6-Cl) | |

C. EXAMPLES OF THE BIOLOGICAL ACTION

Example 1

Filter paper strips (10 mm wide, 90 mm long) were wetted uniformly with the formulated active compounds of the formula I using a concentration of 500 ppm of active compound (about 200 μl/strip) and placed in an agar medium, the type of which depends on the fungus species. 0.5 ml of a suspension culture of the test organism (about $10^5$–$10^6$ conidia/ml) was added to the agar, still in the liquid state, in each petri dish, and the agar plates thus treated were subsequently incubated at 25° C. After inoculation for 3–4 days, the incubation zones were measured and the action of the test substances was evaluated from the inhibition zones formed.

TABLE I

Botrytis cinerea BCM - and iprodione-sensitive (s) and -resistant (r) strain

| Compounds from Example | Inhibition zones in mm at 500 ppm of active compound | |
|---|---|---|
| | s | r |
| 17 | 30 | 22 |
| 27 | 30 | 26 |
| Control | 0 | 0 |

Example 2

Field beans were cultivated at about 26°–28° C. and 60% relative atmospheric humidity. The plants were suitable for the experiments 14 days after sowing (growth height 13–16 cm).

After preparing the plants for the experiment, the experiment preparations were applied to the leaves of the field beans at a concentration of 500 ppm using a glass sprayer at an excess pressure of 0.3–0.5 bar. The treated plants were left to dry and inoculated about 3 hours later.

Spore suspensions containing $4\times 10^5$ spores per ml were prepared using the fresh conidia. The spore suspensions were subsequently applied evenly to the Vicia faba plants with the aid of a fine-spraying glass sprayer, and the plants were placed in a climatic chamber at 20°–22° C. and about 99% relative atmospheric humidity. Infection of the plants was apparent from formation of black spots on leaves and stalks, allowing the plants to collapse in the case of severe infestation.

The experiments were evaluated 3 or 6 days after inoculation. The degree of action of the active compounds was expressed in % compared to the untreated, infected

TABLE II

| Compounds from Example | Degree of action in % at 500 ppm of active compound BCM - and iprodion-sensitive (s) and - resistant (r) strain | |
|---|---|---|
| | s | r |
| 17 | 100 | 100 |
| 27 | 100 | 100 |

TABLE II-continued

| Compounds from Example | Degree of action in % at 500 ppm of active compound BCM - and iprodion-sensitive (s) and - resistant (r) strain | |
|---|---|---|
| | s | r |
| Control | 0 | 0 |

Example 3

Vine seedlings of the "Riesling/Ehrenfelder" types were treated, about 6 weeks after sowing, until dripping wet with aqueous suspensions of the compounds claimed. The application concentrations were 500 and 250 mg of active compound per liter of spray liquor.

After the spray coating had dried, the plants were inoculated with a zoosporangia suspension of Plasmopara viticola and transferred, dripping wet, into a climatic chamber at a temperature of about 23° C. and about 80–90% atmospheric humidity.

After an incubation time of 7 days, the plants were left overnight in the climatic chamber, and the disease was caused to break out. The infestation was subsequently evaluated. The degree of infestation was expressed in % of infested leaf area compared to the untreated, infected control plants, and is reproduced in Table III.

TABLE III

| Example No. | leaf area infected with Plasmopara viticola in % at mg of active compound/liter of spray liquor | |
|---|---|---|
| | 500 | 250 |
| 18 | 0 | 0 |
| untreated, infected plants | 100 | |

Example 4

Wheat plants at the 3-leaf stage were heavily inoculated with conidia of wheat mildew (Erysiphe graminis) and placed in a greenhouse at 20° C. and 90–95% relative atmospheric humidity. One day after inoculation, the plants were wetted evenly with the compounds listed in Table 4 at the active compound concentrations. After an incubation time of 10 days, the plants were investigated for infestation by wheat mildew. The degree of infestation was expressed in % of infected leaf area, relative to untreated, infected control plants (=100% infestation). The result was collated in Table IV.

TABLE IV

| Example No. | leaf area infected with wheat mildew in % at mg of active compound/liter of spray liquor | | | | |
|---|---|---|---|---|---|
| | 500 | 250 | 125 | 60 | 30 |
| 53 | 0 | 0 | 0 | 0 | 0 |
| 54 | 0 | 0 | 0 | 0 | 0 |
| 55 | 0 | 0 | 0 | 0 | 0 |
| 52 | 0 | 0 | 0 | 0 | 0 |
| 17 | 0 | 0 | 0 | 0 | 0 |
| 27 | 0 | 0 | 0 | 0 | 0 |

TABLE IV-continued

| Example No. | leaf area infected with wheat mildew in % at mg of active compound/liter of spray liquor | | | | |
|---|---|---|---|---|---|
| | 500 | 250 | 125 | 60 | 30 |
| 88 | 0 | 0 | 0 | 0 | 0 |
| 30 | 0 | 0 | 0 | 0 | 0 |
| 35 | 0 | 0 | 0 | 0 | 0 |
| 7 | 0 | 0 | 0 | 0 | 0 |
| 89 | 0 | 0 | 0 | 0 | 0 |
| 91 | 0 | 0 | 0 | 0 | 0–3 |
| 94 | 0 | 0 | 0 | 0 | 0 |
| 95 | 0 | 0 | 0 | 0 | 0–3 |
| untreated, infected plants | | | 100 | | |

Example 5

Barley plants (Igri) at the 3-leaf stage were heavily inoculated with conidia of barley mildew (*Erysiphe graminis hordei*) and placed in a greenhouse at 20° C. and 40–60% relative atmospheric humidity. One day after inoculation, the plants were wetted evenly with the compounds listed in Table V, at the active compound concentrations specified. After an incubation time of 10 days, the plants were investigated for infestation by barley mildew. The degree of infestation was expressed in % of infected leaf area, relative to untreated, infected control plants (=100% infestation). The result is collated in Table V.

TABLE V

| Example No. | leaf area infected with barley mildew in % at mg of active compound/liter of spray liquor | | |
|---|---|---|---|
| | 500 | 250 | 125 |
| 51 | 0 | 0 | 0–3 |
| 54 | 0 | 0 | 0 |
| 55 | 0 | 0 | 0 |
| 52 | 0 | 0 | 0–3 |
| 30 | 0 | 0 | 0–3 |
| 94 | 0 | 0–3 | 0–3 |
| 95 | 0 | 0 | 0–3 |
| untreated, infected plants | | 100 | |

Example 6

Cucumber plants (Delikatess type) at the 2-leaf stage were heavily inoculated with a conidia suspension of cucumber mildew (*Erysiphe cichoracearum*). After a drying time of the spore suspension of 30 minutes, the plants were placed in a greenhouse at 22° C. and 90% relative atmospheric humidity.

3 days after infection, the plants were wetted evenly until dripping wet with the active compound concentrations mentioned in Table VI. Assessment took place after 10 days. The degree of infestation was expressed in % of infected leaf area, relative to untreated, infected control plants (=100% infestation). The result was collated in Table VI.

TABLE VI

| Example No. | leaf area infected with cucumber mildew in % at mg of active compound/liter of spray liquor | | | | |
|---|---|---|---|---|---|
| | 500 | 250 | 125 | 60 | 30 |
| 26 | 0 | 0 | 0 | 0 | 0–3 |
| 88 | 0 | 0 | 0 | 0 | 0 |
| 35 | 0 | 0 | 0 | 0 | 0 |
| 31 | 0 | 0 | 0 | 0 | 0–3 |
| 77 | 0 | 0 | 0 | 0 | 0–3 |
| 89 | 0 | 0 | 0 | 0 | 0 |
| 91 | 0 | 0 | 0 | 0 | 0 |
| untreated, infected plants | | | 100 | | |

Example 7

Apple seedlings ("*Malus commuis*"), about 6 weeks old, were wetted uniformly with the active compound concentrations specified in Table VII. After the spray liquor had dried, the plants were wetted evenly until dripping wet with a spore suspension of *Venturia inaequalis* and placed for 48 hours in a dark climatic chamber at a temperature of 20° C. and 100% relative atmospheric humidity.

The plants were subsequently placed in a greenhouse at a temperature of 15°–17° C. and about 100% relative atmospheric humidity infestation evaluation took place about 2 weeks after inoculation. The degree of infestation of the plants with apple scab was expressed in % of infected leaf area, relative to untreated, infected plants, and is reproduced in Table VII.

TABLE VII

| Example No. | % of scab infestation at mg of active compound/liter of spray liquor | | | |
|---|---|---|---|---|
| | 500 | 250 | 125 | 60 |
| 54 | 0 | 0 | 0 | 0 |
| 30 | 0 | 0 | 0 | 0 |
| 35 | 0 | 0 | 0 | 0 |
| 2 | 0 | 0 | 0 | 0 |
| 38 | 0 | 0 | 0 | 0 |
| 7 | 0 | 0 | 0 | 0 |
| 32 | 0 | 0 | 0 | 0 |
| 90 | 0 | 0 | 0 | 0–3 |
| untreated, infected plants | | 100 | | |

Example 8

Wheat plants ("Jubilar") at the 2-leaf stage were wetted uniformly with the active compound concentrations specified in Table VIII. After the spray liquor had dried, the plants were wetted evenly until dripping wet with a spore suspension of *Leptosphaeria nodorum* and placed for 48 hours in a dark climatic chamber at a temperature of 25° C. and 100% relative atmospheric humidity.

The plants were subsequently transferred into a greenhouse at a temperature of 22°–25° C. and about 90% relative atmospheric humidity. Infestation evaluation took place about 1 week after inoculation. The degree of infestation was expressed in % of infected leaf area, relative to untreated, infected control plants (=100% infestation). The result is collated in Table VIII.

TABLE VIII

| Example No. | leaf area infected with Leptosphaeria nodorum in % at mg of active compound/liter of spray liquor | | |
|---|---|---|---|
| | 500 | 250 | 125 |
| 17 | 0 | 0 | 0 |
| 27 | 0 | 0 | 0 |
| 88 | 0 | 0 | 0 |

TABLE VIII-continued

| Example No. | leaf area infected with Leptosphaeria nodorum in % at mg of active compound/liter of spray liquor | | |
|---|---|---|---|
| | 500 | 250 | 125 |
| 30 | 0 | 0 | 0 |
| 35 | 0 | 0 | 0 |
| 94 | 0 | 0 | 0 |
| 95 | 0 | 0 | 0 |
| untreated, infected plants | | 100 | |

Example 9

Field beans ("Herz Freya" or "Frank's Ackerperle" types) were cultivated at about 20° C. and 60% relative atmospheric humidity. The plants were suitable for the experiments 14 days after sowing (growth height 13–16 cm).

After preparing the plants for the experiment, application of the experiment preparations took place at the concentrations specified in Table IX. The treated plants were left to dry and inoculated about 3 hours later.

Spore suspensions containing $1.5 \times 10^6$ spores per ml were prepared using the fresh conidia. The spore suspension was subsequently applied evenly to the *Vicia faba* plants with the aid of a fine-spraying glass sprayer, and the plants were placed in a climatic chamber at 20°–22° C. and about 90% relative atmospheric humidity. Infection of the plants was apparent from formation of black spots on the leaves and stalks, allowing the plants to collapse in the case of severe infestation. Evaluation of the experiment took place about 1 week after inoculation.

The degree of action of the test substances was expressed as a percentage compared to the untreated, infected control.

TABLE IX

| Example No. | Degree of action in % at mg of active compound/liter of spray liquor for BCM - and Iprodion-sensitive (s) and - resistant (r) strain | | | | | |
|---|---|---|---|---|---|---|
| | (s) | | | (r) | | |
| | 500 | 250 | 125 | 500 | 250 | 125 |
| 17 | 97 | 95 | 85 | 95 | 90 | 85 |
| 27 | 90 | 90 | 90 | 95 | 95 | 90 |
| 30 | 85 | 85 | 85 | 85 | 85 | 85 |
| 90 | 90 | 85 | 85 | 90 | 85 | 85 |
| untreated, infected plants | 0 | 0 | 0 | 0 | 0 | 0 |

We claim:

1. A compound of formula I

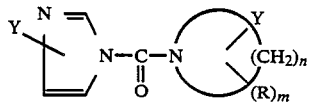

in which
n is 2, 3, 4, 5 or 6,
m is 1 or 2,
R is $-OR^1$, $-\underset{R^2}{\overset{|}{C}}HO-R^1$, $-\underset{R^2}{\overset{|}{C}}H-SR^1$, $-\underset{R^2}{\overset{|}{C}}H_2CHOR^1$, or $-CH_2CH_2CH_2OR^1$, $R^1$ is $(C_1-C_{10})$-alkyl or $(C_3-C_{10})$-alkenyl, each of which is unsubstituted or substituted by 1 to 6 fluorine, chlorine or bromine atoms, hydroxyl, $(C_1-C_4)$-alkoxy, phenyl or phenoxy, where the latter two are unsubstituted or substituted by halogen, $(C_1-C_4)$alkyl or $(C_1-C_4)$alkoxy; or is $C_3$-alkynyl, $(C_3-C_6)$-cycloalkyl, $(C_5-C_6)$-cycloalkenyl, phenyl, benzyl, benzohydryl, trityl, biphenyl, phenoxyphenyl, phenylthiophenyl, naphthyl, 1,2,3,4-tetrahydronaphthyl, indanyl, fluorenyl, pyridyl, benzothiazolyl, benzoxazolyl, quinolinyl, thiochromanyl, benzofuranylmethyl, quinolinylmethyl or phenacyl, where the ring systems mentioned are unsubstituted or substituted by 1–5 substitutents selected from the group consisting of halogen, $(C_1-C_8)$-alkyl, halo($C_1-C_8$)-alkyl, $(C_3-C_8)$-cycloalkyl, $(C_1-C_8)$-alkoxy, halo-$(C_1-C_8)$alkoxy, $(C_3-C_8)$-cycloalkyl$(C_1-C_4)$alkyl, $(C_1-C_8)$alkylthio, halo($C_1-C_4$)alkylthio, $(C_1-C_8)$-alkylsulfinyl, $(C_1-C_8)$alkylsulfonyl, $NO_2$, $-CN$, $-CHO$ and $(C_1-C_4)$alkylcarbonyl; or is $(C_4-C_{10})$-alkadienyl,
$R^2$ is hydrogen or $(C_1-C_4)$alkyl, and
Y is hydrogen, $(C_1-C_4)$alkyl, phenyl or halophenyl where the Y substituents shown in formula (I) are the same or different, and metal-salt complexes thereof.

2. A compound as claimed in claim 1, wherein Y is hydrogen, n is 4 or 5, m is 1, R is $OR^1$, $CH_2OR^1$ or $CH_2CH_2OR^1$, and $R^1$ is phenyl, benzyl, benzohydryl, biphenyl, pyridyl or quinolyl, where the ring systems mentioned are unsubstituted or substituted by 1–3 substituents selected from the group consisting of F, Cl, Br, $(C_1-C_3)$-alkyl, halo($C_1-C_3$)alkyl, $(C_1-C_3)$-alkoxy, halo($C_1-C_3$)alkoxy, $(C_1-C_3)$-alkylthio, $CF_3S$, $CF_3CH_2S$, $NO_2$, $CN$, $CHO$ and $-COCH_3$, and metal-salt complexes thereof.

3. The compound which is 2-(4-trifluoromethylphenoxyethyl)-1-(1-imidazolylcarbonyl)-piperidine.

4. A compound as recited in claim 1, wherein said metal of said metal-salt complex is copper, zinc, tin or manganese.

5. A fungicidal composition comprising an effective amount of a compound as claimed in claim 1 and a suitable carrier.

6. A process for combatting harmful fungi which comprises applying an effective amount of a compound as claimed in claim 1 to said harmful fungi, to a plant in need of protection from said harmful fungi, to a cultivated area of said plant or to a substrate.

* * * * *